United States Patent [19]

Inagami et al.

[11] Patent Number: 4,661,126

[45] Date of Patent: Apr. 28, 1987

[54] STERILIZING PROCESS

[75] Inventors: Kaoru Inagami, Tokyo; Takawo Ohtsu, Kanagawa, both of Japan

[73] Assignees: The Calpis Food Industry Co., Ltd.; JGC Corporation, both of Tokyo, Japan

[21] Appl. No.: 805,291

[22] Filed: Dec. 5, 1985

[51] Int. Cl.$^4$ .............................................. B01D 46/00
[52] U.S. Cl. .......................................... 55/97; 55/279; 55/267; 422/4
[58] Field of Search ............... 55/97, 80, 98, 267–269, 55/279; 422/4, 21, 22, 28, 38; 128/203.26, 203.27; 219/381, 360

[56] References Cited

U.S. PATENT DOCUMENTS

| | | | |
|---|---|---|---|
| 3,557,536 | 1/1971 | Ririe | 55/523 |
| 3,858,645 | 1/1975 | Egger | 422/4 |
| 3,881,896 | 5/1975 | Rothmayr et al. | 55/97 |
| 4,019,021 | 4/1977 | Schladitz | 219/381 |
| 4,235,220 | 11/1980 | Hepner | 55/208 |
| 4,264,346 | 4/1981 | Mann | 55/523 |
| 4,310,747 | 1/1982 | Rice et al. | 219/381 |
| 4,331,454 | 5/1982 | Sweeney | 55/208 |
| 4,444,574 | 4/1984 | Tradewell et al. | 55/97 |

FOREIGN PATENT DOCUMENTS 60-25524  2/1985  Japan ........................... 422/4

OTHER PUBLICATIONS

"Practice for Culturing a Large Amount of DNA-Recombined Microorganisms", *Kagaku Kogaku Technical Report*, No. 3, Chem. Ind. Assn., Nov. 10, 1983.

*Primary Examiner*—Bernard Nozick
*Attorney, Agent, or Firm*—Browdy and Neimark

[57] ABSTRACT

Feed and/or exhaust air can be readily and effectively sterilized by passing said air through a high-temperature filter equipped with built-in heat-retaining material, which process is available in air supply and/or exhaust systems of, e.g., culture equipment for microorganisms and clean rooms in hospitals.

2 Claims, No Drawings

STERILIZING PROCESS

FIELD OF THE INVENTION

This invention relates to a process for readily and effectively sterilizing feed and/or exhaust air.

BACKGROUND OF THE INVENTION

The need for reducing or removing microorganisms contained in feed and/or exhaust air has been recently enhanced. Those generally called microbiologically clean rooms should be equipped with a device for sterilizing feed and/or exhaust air.

In particular, culture chambers for microorganisms, animal cells or plant cells and breeding rooms should be equipped with a cleaning device of a completely containment type.

For example, culture chambers for novel organisms obtained by a recombination of DNA or, pathogenic bacteria or viruses, and breeding rooms for animals having pathogenic bacteria should be equipped with a containment device on a P-3 or P-4 level. In these cases, it is necessary to remove all microorganisms, animal cells, and plant cells present in the exhaust air discharged from the culture chambers or breeding rooms.

On the other hand, food plants, pharmaceutical plants where microbiologically good manufacturing practice (generally referred to as GMP) is required, and operation rooms and infant rooms in hospitals should be equipped with devices for removing organisms in the feed air.

Sterilization of feed and/or exhaust air or microbiologically clean rooms and culture devices has been conventionally performed with a device comprising a filter layer having fine clearances. In exhaust systems wherein high security is required, filtration is carried out by using such a filter above-mentioned as a HEPA filter, being followed by incineration in an incinerator. However the removing ratio achieved by filtering is estimated to be 99.99+% while that achieved by filtering followed by incineration is estimated to be 99.999+%.

Different from other chemical contaminants, contaminating microorganism should be removed at a ratio of 100%. However this technical problem remains open.

Isao Endo has reported that the HEPA filter should be replaced by a more convenient and inexpensive filter and the frequency of its exchange should be examined in order to improve the treatment of exhaust air, thus proposing the necessity of establishing a sterilizing process (cf. Practice for culturing a large amount of DNA-recombined microorganisms", Kagaku Kogaku Technical Report, No. 3, the Chemical Industry Association, Nov. 10, 1983).

Under these circumstances, we have carried out studies on a process for effectively and readily sterilizing feed and/or exhaust air with a convenient device.

At first, we examined various processes for sterilizing feed and/or exhaust air, such as incineration, filtration, passage through a strong alkaline solution, passage through sterilizing shower, and ultraviolet sterilization. However each process so far tested has some disadvantages such that it requires large equipment which makes the process very expensive, that it is a tedious process or that it exhibits an insufficient sterilizing effect. In particular, the filter usually employed in the filter layer is expensive and tends to clog under highly humid conditions to thereby decrease the filter capacity. We have paid our attention to the incineration process which exhibits the highest sterilizing effect among these processes as described above and tried to overcome its disadvantages.

The incineration process is designed to perform in an incinerator or with an electric heater. Incineration in an incinerator makes it possible to treat feed and/or exhaust air at a high temperature.

However it has a disadvantage. That is, the residence time in the high-temperature zone is so short that the formed aerosol would pass therethrough in an unbroken state, thus leaving microorganisms intact in the feed and/or exhaust air though the number of the microorganisms thus left is very small.

On the other hand, in the case of an electric heater it was reported that complete sterilization can be achieved by using an extended heating part at a high temperature of approximately 500° C. (cf. Hakko to Kogyo, vol. 42, No. 1, 9-15, 1984). However the result of our experiment revealed that in the case of a highly humid air, the aerosol might sometimes pass through even at such a high temperature in an unbroken state so that microorganisms are left intact as in the case of the incineration process with the use of an incinerator. It is preferable to employ a heating temperature as low as possible from both safety and economical viewpoints.

SUMMARY OF THE INVENTION

We performed various experiments in order to overcome these disadvantages. As a result, we have found that sufficient sterilization can be achieved at lower temperatures than in the incineration process by using a high-temperature filter equipped with built-in heat-retaining material which accelerates the temperature rise of a passing stream, compared with conventional incineration processes, and completely breaks the aerosol by preventing "fukinuke", thus completing the present invention. The term "fukinuke" means the state that air which must be sterilized passes through a sterilizing device, and goes out of it, with a part of the microorganisms contained in the aerosol surviving. In other words, it means leakage of living microorganisms.

Accordingly the present invention provides a process for sterilizing feed and/or exhaust air with the use of a high-temperature filter equipped with built-in heat-retaining material.

DETAILED DESCRIPTION OF THE INVENTION

The high-temperature filter used in the present invention is a device that is suitable for sterilizing an air stream which is passed therethrough, that can rapidly raise the temperature of the stream to the desired level, that allows the stream to pass therethrough, taking a desired residence time without causing "fukinuke", and that is equipped with built-in heat-retaining material.

In the present invention the internal temperature of the high-temperature filter must be in the range of 225°-400° C., and accordingly the temperature of the heat-retaining material built-in is the same.

The heat-retaining material is a heat-retaining solid having a large heat-resistance and heat-capacity, of which the form is, e.g., granular, reticular and honeycomb, and is at least one material selected from among ceramics, metals, carbon, and minerals, namely these are respectively used alone or in combination in the present invention.

The heat-retaining material is provided in the duct of the filter to thereby maintain the temperature at a desired level. It is preferable that the heat-retaining material has a complicated and dense structure in order to rapidly and uniformly raise the temperature of a stream passing through the filter, and to readily break the formed aerosol. For example, a structure having fine pores or a reticular structure may be appropriate. The heat-retaining material may be directly heated by, e.g., applying an electric current. Alternatively, heating indirectly the heat-retaining material is employable. For example, the heat-retaining material may be given heat from the outside of the high-temperature filter by means of a heater, e.g., electric, oil, and gas heaters.

The temperature and residence time of the air stream should be determined depending on the required cleanness, i.e., the permissible level of the number of bacteria in a certain volume of the air, the amount and rate of aeration, the structure of the device, etc. They may be readily determined by the convenient calibration means as will be described in Experimental Example hereinbelow or similar methods.

The high-temperature filter may be used either as a device on a P-3 or P-4 level wherein a high capability of sterilization is required or as a device on a medium or low level, for example, a highly humid ventilation system such as a conventional fermentation tank wherein nonpathogenic bacteria are used. When bacteria should be removed on a high level, it is preferable to use the high-temperature filter capable of enduring a temperature of 325° C. or above.

An electrical resistance heater or a high-frequency heater is preferable as a heat source of the high-temperature filter of the present invention from the standpoint of safety and operation, though not limited thereto. Other heat sources such as petroleum or gaseous fuels may be used to set the internal temperature of the filter to the desired level. The electrical resistance heater which can be employed includes those generating heat by applying an electric current, such as porous carbon, carbon fiber, ceramics or combinations thereof or conventional ones such as a nichrome wire. Examples of the porous carbon are a molded vitreous article having continuous pores of $1\mu$ to 5 mm in diameter and carbon particles packed in a tube.

An example of the carbon fiber is a bundle of fine carbon fibers.

To further illustrate the high-temperature filter of the present invention, and not by way of limitation, the following examples will be given.

The first example is a high-temperature filter comprising a metal wire packed in a metal tube which is heated with an external heater.

The second example is a high-temperature filter comprising an electrically heated wire or plate and course porous ceramic particles therearound both packed in a metal or ceramic tube which is heated by applying an electric current.

The third example is a high-temperature filter comprising an iron gauze as the heat-retaining material which is heated by high-frequency electricity.

The fourth example is a high-temperature filter comprising a porous carbon sealed in a ceramic tube which is heated by applying an electric current between both ends of the tube as electrodes.

The fifth example is a high-temperature filter comprising carbon fiber sealed in a ceramic tube which is heated by applying an electric current between both ends of the tube as electrodes.

In the fourth and fifth examples, the porous carbon and the carbon fiber serve each as a heater as well as the heat-retaining material because of its porous or reticular structure so that it is not necessary to employ the additional heat-retaining material in these cases. Further these two filters make it possible to use the whole internal part as a heater so that the internal temperature can be rapidly and uniformly set to the desired level. Furthermore the uniform and dense internal structure thereof would significantly prevent "fukinuke", thus making it easy to break the aerosol.

The temperature of the air stream may be measured with a thermometer. However the temperature may vary with a change in the flow of the stream or in the moisture content thereof. Therefore it is preferable to maintain the desired temperature by varying the electric voltage with an automatic thermostat. In addition, an external heat insulating device is required to maintain the safety.

The high-temperature filter is further equipped with a device for preventing overheating if necessary.

It is possible to connect the high-temperature filters in series to thereby enhance the sterilizing effect.

The high-temperature filter of the present invention may be used not only in preventing microorganisms in an exhaust system from scattering but also in preventing microbial contamination in a clean area. In the case of an exhaust system, it is preferable that the internal pressure is higher than that of the external atmosphere. For example, there is no problem in the case of a microbial culture device since the internal pressure is high. In the case of a ventilating system of a clean area, a cooling device should be mounted if necessary, since the temperature of an air stream entering the system is high.

The process of the present invention may be applied to exhaust systems wherein a high safety level is required and to air supply and/or exhaust systems of, e.g., food plants, pharmaceutical plants where GMP is required, clean rooms in hospitals, culture devices for microorganisms, animal cells or plant cells, and breeding rooms.

Thus the process of the present invention is a novel sterilizing process wherein the internal temperature of the filter can be safely controlled to a lower level than that of conventional incineration processes and the aerosol is broken by extending the period of contact with microorganisms contained in the feed and/or exhaust air and by preventing "fukinuke", thus enhancing the sterilizing efficiency.

Now the present invention will be described in more detail by reference to a model experiment conducted by us. This experiment was performed in order to determine the minimum temperature required for the high-temperature filter and to determine the sterilizing effect of the high-temperature filter.

EXPERIMENTAL EXAMPLE

A heat-resistant glass tube of 19 mm in internal diameter and 200 mm in length was externally coated to insulate heat and a cylindrical molded product (19 mm in external diameter and 170 mm in length) of porous carbon of approximately 0.1 mm in pore size was heated in the tube. A lead wire was stuck on each end of the porous carbon with carbon cement. A temperature sensor was mounted at the center of said porous carbon. An electric current was applied through the lead wires to thereby heat the porous carbon to the desired temperature. The high-temperature filter was connected to a temperature cushioning tube comprising glass wool roughly packed in a glass tube of 19 mm in internal diameter and 200 mm in length, and a coiled glass condenser of 300 mm in length was connected to this tube. Then a glass culture flask of 1 l with two side-tubes each having a cotton plug and a thermometer was connected to the condenser at one of said two side-tubes. An ordinary cotton plug was provided in another opening of said high-temperature filter. Thus a device comprising cotton plug/high-temperature filter/glass wool tube/coiled condenser/culture flask was constructed. Approximately 200 ml of a conventional microbial medium comprising glucose, yeast extract, a mixture of inorganic salts and agar was introduced into the culture flask and the whole device was sterilized by heating at 134° C. for 15 min in an autoclave.

Separately, 4 l of a culturing broth for yeasts was introduced into a culture tank of 10 l and stirred at 100 rpm under sterile aeration to thereby prepare equipment for culturing Saccharomyces cerevisiae at 27° C. After removing the cotton plug, the high-temperature filter device was connected to the exhaust vent of the culture equipment under a sterile condition. Prior to the connection, cold water was passed through the condenser and the temperature at the center of the filter was set to the test temperature. Aeration was performed from the blowing hole of the 10 l culture tank. A flow meter was mounted onto the other side-tube (i.e. exhaust vent) with the cotton plug of the 1 l culture flask to thereby control the aeration to give a particular flow. Thus the whole device was designed to examine the condition in the culture flask, which was sterile at first, after introducing the aerosol containing the yeast and formed by the aeration and stirring in the culture tank via the high-temperature filter. During the experiment, the temperature of the culture flask was carefully controlled not to exceed 30° C. Table 1 shows the result of observation on yeast colonies appearing in the solid medium in the culture flask after culturing the yeast under aeration for 10 hours and maintaining it at 27° C. for seven days. Each filter temperature refers to the one determined with the sensor at the center of the filter. A control experiment was carried out wherein the high-temperature filter was replaced with a device composed of a spiral nichrome wire of 0.45 mm in diameter and 2,000 mm in length inserted into a heat-resistant glass tube of 19 mm in internal diameter and 200 mm in length externally coated to insulate heat. The result is also shown in Table 1.

The result of this experiment suggests that the process of the present invention wherein aeration is performed at a flow rate of 0.85 ml/sec, which results in an average residence time in the high-temperature filter of approximately 60 sec, is effective at 225° C. and available in clean rooms of a low level such as those in food plants.

When aeration is carried out at 4.25 ml/sec, which results in an average residence time in the high-temperature filter of approximately 12 sec, a temperature of 300° C. or above would bring about an effective result. However it seems necessary to raise the temperature approximately to 350° C. to give a complete sterilizing effect. As shown in Table 1, two high-temperature filters simultaneously used in series were effective even at a flow rate of 17 ml/sec at 300° C.

These facts suggest that contamination with microorganisms can be prevented by raising the temperature of the high-temperature filter to at least a certain level.

After repeating several times similar experiments including those wherein other microorganism (Escherichia coli) was employed, it has been found that the minimum temperature required for the high-temperature filter is 225° C. at the center of the filter, which results in a residence time in the high-temperature filter of approximately 60 sec. It has been further found that at a high aeration rate sterilization can be achieved at lower temperatures by employing the long high-temperature filter or employing a plurality of the high-temperature filters.

In the case of the control experiment wherein no high-temperature filter was used, yeast colonies were observed even at a high temperature of 350° C. indicating a lower sterilizing effect than that of the process of the present invention.

What is claimed is:

1. A process for sterilizing feed or exhaust air by heating, which comprises:
   directly heating a high-temperature filter including built-in heat-retaining material by the application of electric current to said heat-retaining material to bring the temperature of the heat-retaining material into a range of 225° to 300° C., the heat-retaining material being at least one material selected from the group consisting of ceramics, carbon fiber, and porous carbon; and
   passing said air through said heated high-temperature filter.

2. The process of claim 1, wherein said at least one material is selected from the group consisting of porous carbon and carbon fiber.

TABLE 1

| | Bactericidal degree (Yeast colony count) | | | | | |
|---|---|---|---|---|---|---|
| | High-temperature filter (single) | | | | High-temperature filter (double) | |
| | Aeration (0.85 ml/sec) | | Aeration (4.25 ml/sec) | | Aeration (17 ml/sec) | |
| Filter temperature | Expt. of invention | Control expt. | Expt. of invention | Control expt. | Expt. of invention | Control expt. |
| Not heated | +++ | | +++ | | +++ | |
| 200° C. | ++ | +++ | +++ | +++ | ++ | +++ |
| 225° C. | +~- | +++ | ++ | +++ | + | +++ |
| 250° C. | - | ++ | + | +++ | + | +++ |
| 275° C. | - | + | + | ++ | +~- | +++ |
| 300° C. | - | + | +~- | ++ | - | ++ |
| 325° C. | - | + | - | + | - | + |
| 350° C. | - | + | - | + | - | + |

+++: High colony count,
++: Medium colony count,
+: Low colony count.
-: None